(12) United States Patent
Opheij et al.

(10) Patent No.: US 10,512,438 B2
(45) Date of Patent: Dec. 24, 2019

(54) MEDICAL IMAGING WITH INTEGRATED AIR GUIDANCE

(71) Applicant: KONINKLIJKE PHILIPS N.V., Eindhoven (NL)

(72) Inventors: Martinus Cornelis Opheij, Sint Oedenrode (NL); Walter Peter Bleyen, Lommel (BE); Paulus Cornelis Luttikhuizen, Veldhoven (NL); Ineke Elisabeth Van Rij, Den Bosch (NL); Rob Van Gils, Diessen (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 204 days.

(21) Appl. No.: 15/544,297

(22) PCT Filed: Jan. 18, 2016

(86) PCT No.: PCT/EP2016/050865
§ 371 (c)(1),
(2) Date: Jul. 18, 2017

(87) PCT Pub. No.: WO2016/116389
PCT Pub. Date: Jul. 28, 2016

(65) Prior Publication Data
US 2018/0008219 A1    Jan. 11, 2018

(30) Foreign Application Priority Data
Jan. 20, 2015 (EP) ..................................... 15151788

(51) Int. Cl.
*A61B 6/00* (2006.01)
*A61G 13/10* (2006.01)

(52) U.S. Cl.
CPC .......... *A61B 6/4423* (2013.01); *A61B 6/4441* (2013.01); *A61B 6/4464* (2013.01); *A61G 13/108* (2013.01)

(58) Field of Classification Search
CPC ... A61B 6/4423; A61B 6/4441; A61B 6/4464; A61B 90/11; A61B 17/0206;
(Continued)

(56) References Cited
U.S. PATENT DOCUMENTS

2001/0030867 A1    10/2001    Gampe
2008/0101546 A1    5/2008    Delmas
(Continued)

FOREIGN PATENT DOCUMENTS

DE    20004384 U1    11/2000
EP    2679213 A2    1/2014
(Continued)

OTHER PUBLICATIONS

"The Freedom you need: Philips Allura Xper RD Family with Flexmove" Mar. 2011.

*Primary Examiner* — David P Porta
*Assistant Examiner* — Fani P Boosalis

(57) ABSTRACT

A medical X-ray imaging arrangement includes an X-ray image acquisition device, a movable carriage, and an air-supply for an operating zone. The carriage is movably mountable to a ceiling of an operating room. The X-ray image acquisition device has an X-ray source, and the X-ray image acquisition device is movably mounted to the movable carriage for acquiring image information of an object. Further, the air-supply includes a plurality of air outlets provided on a bottom side of the carriage arranged to provide treated air from an air-feed as a primary laminar downflow defining a carriage laminar flow zone for the operating zone.

20 Claims, 6 Drawing Sheets

(58) Field of Classification Search
CPC .... A61G 12/004; A61G 13/108; F16M 11/28;
F16M 13/027; A61F 7/0053
See application file for complete search history.

(56) References Cited

U.S. PATENT DOCUMENTS

2012/0281812 A1\* 11/2012 Noda .................... A61B 6/4233
378/62
2013/0344795 A1 12/2013 Schreiber
2015/0342547 A1\* 12/2015 Janssen ................ A61B 6/4464
378/62

FOREIGN PATENT DOCUMENTS

| JP | 2002306461 A | 10/2002 |
|----|--------------|---------|
| WO | 2010082147 A1 | 7/2010 |
| WO | 2014111437 A1 | 7/2014 |

\* cited by examiner

MEDICAL IMAGING WITH INTEGRATED AIR GUIDANCE

CROSS-REFERENCE TO PRIOR APPLICATIONS

This application is the U.S. National Phase application under 35 U.S.C. § 371 of International Application No. PCT/EP2016/050865, filed on Jan. 18, 2016, which claims the benefit of European Patent Application No. 15151788.5, filed on Jan. 20, 2015. These applications are hereby incorporated by reference herein.

FIELD OF THE INVENTION

The present invention relates to a medical X-ray imaging arrangement and to a medical imaging system.

BACKGROUND OF THE INVENTION

In operating rooms, for example in a hospital, air-supply is usually provided for the area or region, in which patient treatment is provided. For example, cleaned air is provided to the patient table and equipment to prevent infection. For this purpose, as an example, a flow of air is provided from a ceiling area in a downward manner, for example as a laminar airflow. During different types of procedure, such as minimally invasive operations or open surgery or other interventional procedures, X-ray imaging may be provided. For X-ray imaging, movable X-ray imaging systems are hence also provided in an operating room. For example, X-ray imaging systems are movably mounted to a ceiling in order to allow a variety of imaging positions in relation to a patient arranged on a patient support. However, the arrangement of an X-ray imaging device may lead to disturbance of the downflow of the air-supply. WO 2014/111437 describes a ceiling suspension system that is mounted to the ceiling in an area besides a laminar flow zone downflow. Nevertheless, it has been shown that such an arrangement still means certain restrictions in the design options of operating areas.

SUMMARY OF THE INVENTION

There may thus be a need to provide an improved air-supply for operating areas.

The object of the present invention is solved by the subject-matter of the independent claims, wherein further embodiments are incorporated in the dependent claims. It should be noted that the following described aspects of the invention apply also for the medical X-ray imaging arrangement and for the medical imaging system.

According to a first aspect of the present invention, a medical X-ray imaging arrangement is provided that comprises an X-ray image acquisition device, a movable carriage, and an air-supply for an operating zone. The carriage is movably mountable to a ceiling structure of an operating room. The X-ray image acquisition device comprises an X-ray source, and the X-ray image acquisition device is movably mounted to the movable carriage for acquiring image information of an object. Further, the air-supply comprises a plurality of air outlets provided on a bottom side of the carriage arranged to provide treated air from an air-feed as a primary laminar downflow defining a carriage laminar flow zone for the operating zone.

By providing the plurality of air outlets on the bottom side of the carriage itself, it is ensured that a downflow of air is provided for the operating zone, in particular for the region of interest of the operating zone, which is the region to be imaged by the X-ray image acquisition device. The plurality of air outlets are provided in an evenly distributed manner across the lower surface of the carriage. The air outlets on the bottom or lower side of the carriage thus ensure that a laminar flow of air from a ceiling, for example, is effectively not blocked by the movable carriage. Rather, the plurality of air outlets thus moves along with the carriage, since the air outlets are provided on the bottom side of the carriage. Hence, a movable air-supply is provided that leads to a laminar flow zone, and can hence so-to-speak compensate for the part of a ceiling airflow where the ceiling airflow would be blocked by the movable carriage when moving the X-ray image acquisition device for achieving a suitable imaging position in relation to the patient.

An air-supply in the form of a ceiling air-supply may thus be provided for a laminar flow throughout the operating zone. By receiving the treated air from atop from the air outlets in the ceiling, the same amount of air, and also same type of air, can be provided in the laminar flow zone below the carriage that is also provided around this zone in form of the laminar flow from the ceiling, i.e. from a ceiling laminar flow zone around the carriage laminar flow zone.

The "operating zone", also referred to as operational zone, is an area or part of an operating room, which is provided for an operation, such as a medical treatment, surgery, minimally invasive surgery or intervention, or other treatment of a patient. Instead of, or in addition to surgical or interventional procedures, also other types of treatment or procedures can be foreseen, such as therapeutic procedures or examining procedures or diagnostic procedures. As a general aspect, specific requirements in terms of hygienic conditions are made for these zones or areas. These requirements include the demand for a clean air supply in the operating zone, e.g. to provide and/or maintain sterile conditions.

The ceiling structure can be a ceiling of a room or can be a support structure arranged overhead, but supported by (side-) wall structures, such as transverse beams.

In an example, an equipment-carrying device is provided, and the equipment-carrying device is suspendably mounted to the carriage. Further, the X-ray image acquisition device is movably mounted to the equipment-carrying device.

According to an example, the carriage comprises an air inlet that is connectable to the air-feed. Further, preferably a distribution zone is provided as a hollow space that extends transverse to a flow direction and that connects the air inlet with the plurality of air outlets. In an example, the distribution zone extends substantially along a dimension of the carriage, i.e. along the length of the carriage being its dimension in a direction in which the carriage moves along the ceiling structure when mounted thereto, and/or along the width of the carriage being its dimension transverse to such movement direction.

According to one example, a laminar air filter is provided to be arranged downstream the distribution zone. At least a part of a downstream side of the laminar air filter forms the plurality of air outlets.

According to one example, the air inlet is provided to be arranged on an upper side of the carriage. The air inlet is configured to receive the treated air from a plurality of supply-air outlets provided in a ceiling structure above the medical X-ray imaging arrangement. An airflow passage is provided inside the carriage between the air inlet and the plurality of air outlets.

Preferably, the air inlet comprises a plurality of inlets configured to receive the treated air from at least one supply-air outlet provided in a ceiling structure above the medical X-ray imaging arrangement. In an example, an airflow passage within the carriage comprises a plurality of passageways in connection with the air inlets, which passageways discharge treated air into the distribution zone. The distribution zone thus connects the passageways with the plurality of air outlets at the bottom side of the carriage.

According to another example, the carriage comprises an air inlet conduit for connection with an air-feed. In this example, the distribution zone is arranged as a passageway between the air inlet conduit and the air outlets at the bottom of the carriage.

This allows an air-supply independent from an air-supply of the ceiling, for example when the carriage is rather large. The arrangement provides sufficient laminar flow around the X-ray image acquisition device (or imaging device, or imaging system) and thus provides a large primary laminar downflow.

According to an example, a sealing is provided attached to an edge region of the upper side of the carriage. The sealing is configured to close an air gap between the carriage and a ceiling structure preferably comprising the supply-air outlets, when the carriage is mounted to the ceiling structure. As an option, the sealing may be provided movable to adjustably close or open the air gap.

The sealing ensures that the amount of air provided by an air-supply in the ceiling structure is effectively used for the primary laminar downflow. A movable sealing can be used, for example, for facilitating a relative movement of the movable carriage in relation to the ceiling structure. The gap can be closed only in the fixed position, i.e. during the movement, the sealing can be provided with a distance to the ceiling structure. The movability further allows an adjustment to further control or regulate the airflow from the ceiling structure to the plurality of air outlets.

According to an example, the carriage comprises at least one side skirt air-guiding device. The at least one side skirt air-guiding device is configured to guide treated air from above the carriage i) towards the laminar down flow provided by the plurality of air outlets, and/or ii) towards the air inlet for supplying the air to the distribution zone.

A side skirt can advantageously be used in case the carriage has closed parts, i.e. parts of the carriage, in which a flow of air or air passages cannot be provided. The side skirt advantageously circumvents such closed parts. In one example, the carriage is a closed system and the side skirt is provided on one or more sides of the carriage to arrange for the air supply by guiding air from above to the air inlet for supplying air to the distribution zone. The distribution zone and also, for example, the laminar air filter are arranged below the (closed) carriage.

According to an example, a ventilation device may be provided in the airflow passage within the carriage to support the airflow from the air inlet and the plurality of air outlets.

The ventilation device, for example a fan, allows a further adjustment of the primary laminar downflow. For example, the ventilation device may be used to compensate the flow resistance in the carriage between the air inlets and the air outlets. As another option, the ventilation device can be used to provide a primary laminar downflow with an increased flow of air in relation to the surrounding downflow area.

According to an example, the arrangement further comprises an equipment-carrying device; and, in addition to the movable carriage, also the equipment-carrying device can be provided with an airflow passage and air outlets on its lower side.

This further adds to the primary laminar downflow to be an even air-supply for the operating zone.

According to an example, the X-ray image acquisition device comprises a C-arm X-ray device, which is movably mounted to the movable carriage.

For example, the X-ray image acquisition device is directly mounted to the movable carriage. In another example, the X-ray image acquisition device is mounted to the carriage by an equipment-carrying device.

According to a second aspect, a medical imaging system is provided that comprises a medical X-ray imaging arrangement, a patient support, and a rail arrangement. The medical X-ray imaging arrangement is provided according to one of the above-mentioned examples. The rail arrangement is arranged overhead and disposed above the patient support. The carriage of the medical X-ray imaging arrangement is movably mounted along the rail arrangement. An air-feed is provided for supplying treated air for the laminar downflow.

The "medical imaging system", comprising an X-ray imaging arrangement, can also be referred to as "medical X-ray imaging system".

According to an example, a ceiling region above at least a part of the rail arrangement is provided as the air-feed and comprises a plurality of supply-air outlets.

According to an example, the ceiling region with the supply-air outlets is larger than the carriage, which is movable in relation to the ceiling. The carriage is arranged below the ceiling partly masking, i.e. covering, the supply-air outlets of the ceiling structure. Unmasked, i.e. uncovered, supply-air outlets act as ceiling air outlets. The ceiling air outlets provide a secondary laminar downflow defining an additional laminar flow zone for the operating zone. The carriage laminar flow zone and the additional laminar flow zone provide a laminar downflow covering the operating zone.

According to an aspect of the present invention, the X-ray imaging equipment is movably mounted to a ceiling structure. The X-ray imaging equipment is supported by a movable carriage. The carriage is equipped with an air-supply providing a plurality of air outlets for achieving a laminar downflow from the carriage towards the patient table arranged in the operating zone. In other words, the carriage, which itself represents an obstruction for an airflow from the ceiling towards the floor, is provided as an air-supply. Thus, the effective obstructions of the laminar downflow are reduced to a minimum and the necessity for providing nozzles for forming air jets for providing the downflow are prevented. Hence, an even and regular flow or pattern of airflow is provided throughout the operating zone. The used air can then be disposed elsewhere in the room to ensure that the supply-air and the used air are not mixed. For example, an even flow of air with an average speed of 0.3 m/s (meters per second) may be provided.

These and other aspects of the present invention will become apparent from and be elucidated with reference to the embodiments described hereinafter.

BRIEF DESCRIPTION OF THE DRAWINGS

Exemplary embodiments of the invention will be described in the following with reference to the following drawings.

DETAILED DESCRIPTION OF EMBODIMENTS

Figure 1:
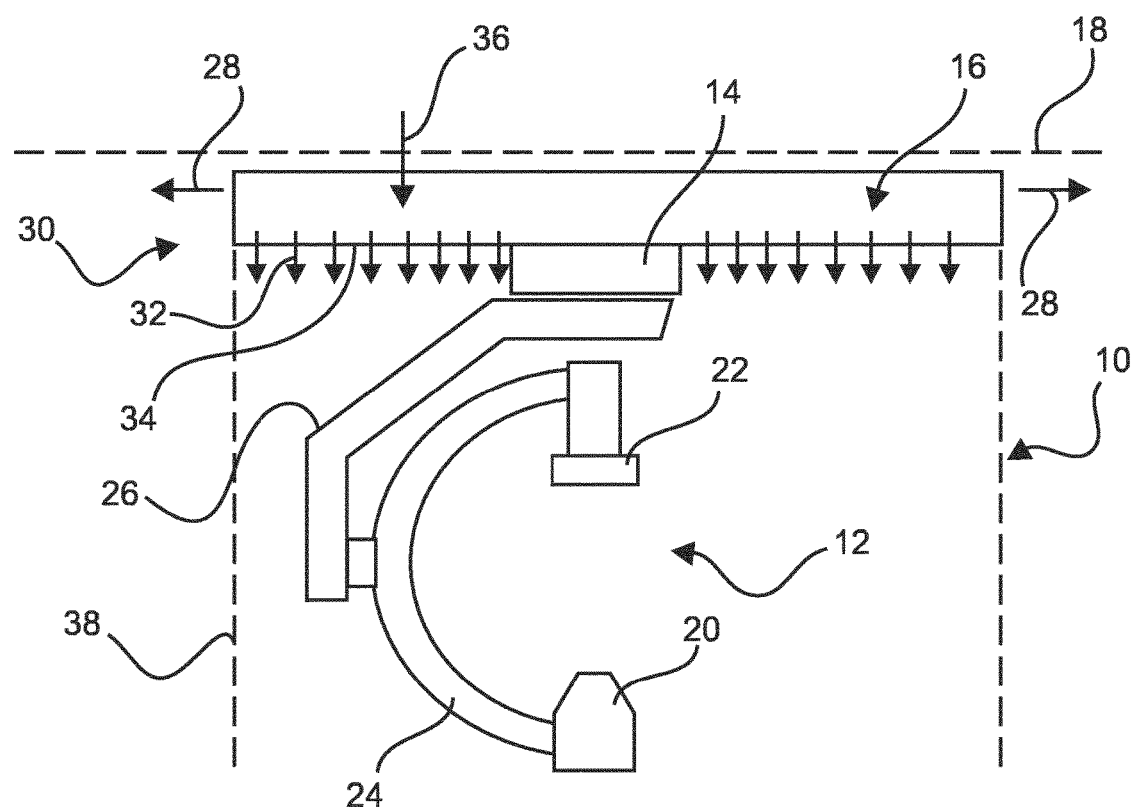
FIG. 1 shows a schematic setup of an example of a medical X-ray imaging arrangement in an elevation view from aside.

FIG. 1 shows a schematic setup of a medical X-ray imaging arrangement 10. The medical X-ray imaging arrangement 10 comprises an X-ray image acquisition device 12, and a movable carriage 16.

The carriage 16 is movably mountable to a ceiling 18, or ceiling structure, of an operating room. The ceiling 18 is indicated with a dotted line in FIG. 1. The X-ray image acquisition device 12 comprises an X-ray source 20. As an option, an X-ray detector 22 is further shown. The X-ray detector 22 and the X-ray source 20 are mounted to a C-arm structure 24, which is also shown as an option.

The X-ray image acquisition device 12 is movably mounted to the movable carriage 16 for acquiring image information of an object. For example, a support arm structure 26 can be provided, with which the C-arm structure 24 is mounted to the movable carriage 16. Hence, the C-arm X-ray device is movably mounted to the movable carriage 16.

As an option, an equipment-carrying device 14 is provided. The equipment-carrying device 14 is suspendably mounted to the carriage 16; and the X-ray image acquisition device 12 is movably mounted to the movable carriage 16 by the equipment-carrying device 14. Hence, the C-arm X-ray device is movably mounted to the equipment-carrying device 14.

It is noted that, although the figures show the equipment-carrying device 14, the X-ray image acquisition device can be directly attached to and supported by the movable carriage 16 without the provision of the equipment-carrying device 14, or indirectly when providing the equipment-carrying device 14. In general, the X-ray imaging equipment is at least partly (i.e. at least the source) movably mounted to the movable carriage for acquiring image information of an object from different directions.

The X-ray image acquisition device can be provided movably in different directions, i.e. along different axes and around different rotation axes, which is not further shown.

Two arrows 28 schematically indicate the movability of the movable carriage 16 in relation to the ceiling 18. Of course, other directions of movement of the movable carriage 16 can be provided, for example in a transverse direction to the arrows 28, i.e. along a transverse direction along the ceiling 18.

Further, an air-supply 30 for an operating zone is provided. The air-supply comprises a plurality of outlets, indicated with small air outlet arrows 32, provided on a bottom side 34 of the carriage 16 arranged to provide treated air from an air-feed as a primary laminar downflow. The air-feed is indicated with a schematic air-feed arrow 36. The primary laminar downflow is defining a carriage laminar flow zone 38, which boundaries are schematically indicated with vertical dotted lines. The carriage laminar flow zone 38 is provided for the operating zone.

In one example (not further shown in detail), the plurality of outlets is provided by a laminar filter that generates the laminar flow. The filter may form a large outer surface, from which the laminar airflow results.

In another example, a downflow filter is provided to be arranged upstream of the air outlets.

In another example (not further shown in detail), the plurality of outlets is provided by individual air nozzles, each providing a part-stream of air. Due to the close vicinity of the generated little part air-streams, a laminar airflow results.

The term "X-ray imaging" relates to irradiating an object with X-rays produced by the X-ray source and to detecting the respective radiation by the X-ray detector.

The "equipment-carrying device" relates to a mounting structure for supporting the actual X-ray imaging equipment, such as the X-ray source. The equipment-carrying device provides the mechanical support and connection of the X-ray image acquisition device (or X-ray imaging equipment or imaging system) to the movable carriage. The equipment-carrying device can also be referred to as mounting structure or support structure. The equipment-carrying device allows a stable positioning of the image acquisition arrangement by providing a mechanical link to the carriage. Stability can be achieved, for example, by a move-and-lock functionality. In an example, the equipment-carrying device is adapted to allow a manual moving by medical staff, or, alternatively or in addition, allows to be moved through motor arrangements. Such motors or drives can be provided, for example, at connection points between the equipment-carrying device and the image acquisition arrangement and/or the rail arrangement. The equipment-carrying device can be designed to be at least partly located in a minimum vertical height over the heads of medical staff or equipment to minimize blocking of space and avoid collisions. A motor-supported manual moving, i.e. a servo-motorized movement may also be provided, as indicated above. In one example, the equipment-carrying device comprises segmented arms, which are connected to each other with hinges. In another example, the equipment-carrying device comprises telescopic arms, which can be driven, for instance, hydraulically or electromagnetically with drives and gear mechanism. It should be noted, that telescopic arms are seen as having at least two structural members or segments.

As indicated above, the function of the equipment-carrying device can also be provided by the movable carriage itself.

In an example, the equipment-carrying device comprises a turntable-shaped rotating bearing. The turntable-shaped rotating bearing may be provided with outer dimensions that are smaller than the size of the movable carriage.

In one example, the movable carriage is provided with an outer size that is at least twice as large as the outer size of the turntable-shaped rotating bearing.

In one example, the equipment-carrying device is mounted to the movable carriage in a fixed manner. As an option, the equipment-carrying device is built in an integrated manner with the movable carriage.

In another example, the equipment-carrying device is mounted to the movable carriage in a movable manner.

The "movable carriage" relates to a mounting structure that connects the equipment-carrying device with a support structure in a movable manner. In an example, the movable carriage is provided for mounting the equipment-carrying device to a rail structure, i.e. an arrangement of several rails, e.g. mounted to a ceiling, such that the carriage can move along the rails, while allowing a secure load transmission, i.e. a secure hold of the weight of the X-ray image acquisition device (or X-ray imaging equipment or X-ray system). The carriage can be a sliding carriage that slides along provided rails.

The "suspendably" mounted relates to a support in a hanging manner. The support structure for holding the X-ray equipment is thus provided overhead.

The "air-supply" relates to the provision or supply of air to the operating zone.

The "air-feed" relates to the provision of supply air, i.e. a source of the supply air that is to be provided or supplied to an operating room. The air-feed may also be referred to as air supply source. The air-feed, or air supply source, generates a stream or flow of air.

The treated air relates to cleaned air, such as sterile air. The air may be conditioned, e.g. adapted in temperature and/or relative humidity.

The air is provided to the operating room in order to ensure or at least support sterility of the operating zone and to a certain extent also the surrounding room portions.

The air is provided e.g. as a laminar airflow in the sense of an airflow with no or minimal turbulences, for providing sterility and clean-room-like conditions to the operating zone in order to minimize negative implications due to unsterile conditions. For example, the laminar airflow is provided in order to keep the operating area sterile also when, for example, heads of doctors and staff are in the airflow. In another example, air-supply outlets are controlled in terms of the area, which area requires such laminar flow. In other words, the air-supply can be displaced or moved, depending on the area of intervention.

The plurality of air outlets may be provided as a mesh-like structure. The outlets may be arranged in a grid-like pattern, or in a random pattern across a surface. In general, the air outlets are provided in such a density that an even and laminar type of airflow is provided.

Sub-portions of the plurality of air outlets may be attached to one or several frames as a grid- or mesh-like structure, and a number of the frames may be used to cover a larger area.

The "operating zone" relates to a part of an operating room, which may also be referred to as operating theatre. The operating zone is a zone configured for medical operations, such as interventions or other treatments, e.g. of patients. The operating zone may be provided in a hospital or medical practice.

The term "laminar flow" relates to a parallel airstream with no or minimal turbulences, supporting sterility in an operation theatre, in particular in the area of the patient support. A laminar flow is usually vertical, downwardly oriented and therefore often described as "downflow". The laminar flow zone is a zone of low-turbulence flow. For example, a maximum speed of air of approximately 1 m/s, for example below 0.7 m/s or below 0.5 m/s is provided, for example 0.3 m/s as an average speed of the airflow. The "carriage laminar flow zone" is an area below the carriage, in which area an even downflow of air is provided. The laminar flow zone is a zone of an even distribution of ventilation.

In an example, the air outlets, or supply-air outlets, comprise an opening or a plurality of openings, such as perforations, channels or the like. The supply-air outlets may be provided as nozzles.

The "bottom side" relates to the underside or undersurface of the carriage, i.e. the surface that faces downwards, i.e. towards the operating zone.

Figure 2:
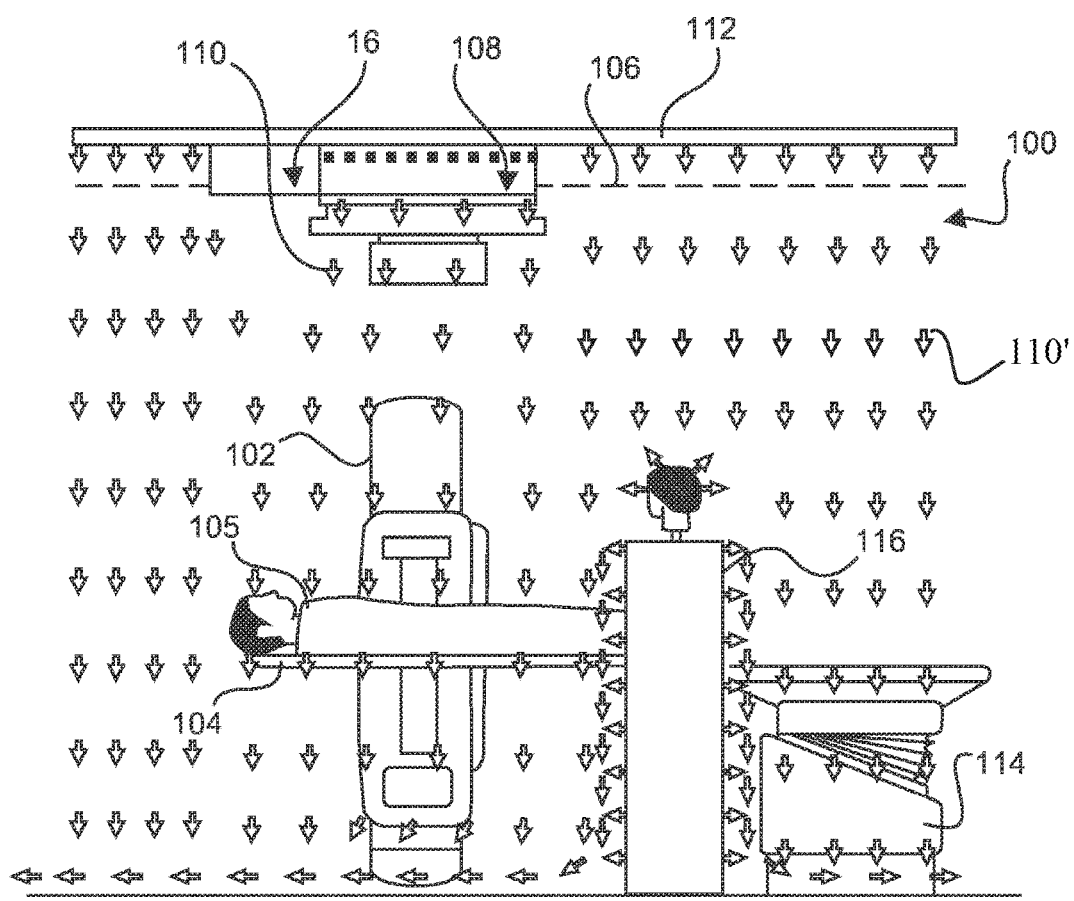
FIG. 2 shows an example of a medical imaging system in a schematic setup.

With reference to FIG. 2, in the following an example of a medical imaging system 100 is described. The medical imaging system 100 comprises a medical imaging arrangement 102 and a patient support 104. A patient 105 is shown arranged on the patient table 104. Further, a rail arrangement 106, indicated with a single horizontal dotted line, is provided. The medical X-ray imaging arrangement 102 is provided according to one of the above-mentioned examples. The medical imaging system 100, comprising the X-ray imaging arrangement 102, can also be referred to as medical X-ray imaging system. The rail arrangement 106 is arranged overhead and disposed over the patient support 104. The carriage, indicated with the reference numeral 16, of the medical X-ray imaging arrangement 102 is movably mounted along the rail arrangement 106. Further, an air-feed 108, indicated with a single air-feed arrow, is provided for supplying treated air for the primary laminar downflow. The primary laminar downflow is schematically indicated with a plurality of small arrows 110. Further, as an option, a ceiling region 112 above at least a part of the rail arrangement is provided as the air-feed and comprises a plurality of air-supply outlets (not further shown in detail). As a further option, the ceiling region 112 with the supply-air outlets is larger than the carriage 16, which is movable in relation to the ceiling. The carriage is arranged below the ceiling partly masking or covering the supply-air outlets of the ceiling structure. Unmasked or uncovered supply-air outlets act as ceiling air outlets. The ceiling air outlets provide a secondary laminar downflow defining an additional laminar flow zone for the operating zone. The carriage laminar flow zone and the additional laminar flow zone provide a laminar downflow covering the operating zone. It is noted that also the secondary laminar downflow is indicated with small arrows 110' in FIG. 2.

Hence, the primary laminar downflow and the secondary laminar downflow provide an operating flow. The carriage laminar flow zone and the additional laminar flow zone provide an additional flow zone.

In FIG. 2, the patient support 104 is provided with a base structure 114 that may be provided to allow adjustment in height and arrangement along horizontal directions and also tilt arrangement for positioning the patient. Further, a staff member 116 is schematically indicated. It is noted that in FIG. 2, the staff member 116 is indicated very schematically and also in combination with little arrows indicating an airflow resulting from (or caused by) the thermal energy due to the presence of the staff member.

The term "rail arrangement" relates to one or more rails, for example arranged in parallel, to allow a movement of a connected part or member along the rails. The rail arrangement can be preferably fixed to the ceiling or to sidewalls or other immobile members in order to provide a stabilizing and supporting effect. The rail arrangement can be, for example, a wheel-rail combination, a sleeve bearing, or other means moving on or along the rails.

A moving along the rail arrangement can be seen as a translational movement by shifting or sliding of the equipment-carrying device on or at the rails. This translation can be combined with a possible pivoting movement or rotation of the equipment-carrying device around a mounting point of the equipment-carrying device at the rail arrangement.

In a further example, not further shown, the ceiling region with air outlets is extending over an area that is covering the patient support plus a determined surrounding zone. The patient support may be provided with dimensions such as approximately 0.5 m (meter) to 1.0 m by 1.5 m to 2.5 m, and the surrounding zone may be provided as a 0.5 m periphery or as a 1.0 m periphery, or as a smaller or larger periphery.

In the following, further examples of the medical X-ray imaging arrangement are described. It is noted that some of these examples are described in relation with the above-mentioned medical imaging system 100, but the particular examples and their features are provided also for the medical X-ray imaging arrangement 10, or as a further option for the medical imaging system 100, although the drawings may show all the features of the medical imaging system 100, or some of the essential features of the medical imaging system 100. In other words, although the examples are shown and described in the context of the medical imaging system 100, they are also provided in the context of the medical X-ray imaging arrangement 10.

According to a further example, the carriage 16 comprises an air inlet 40 that is connectable to the air-feed 36. Further, a distribution zone 60 (see also below) is provided. The distribution zone 60 is a hollow space that extends transverse to a flow direction as represented by arrows 50, 56 and connects the air inlet 40 with the plurality of air outlets 32. The distribution zone may be provided as a pressure chamber, i.e. a space that is used for supplying air in an at least slightly pressurized form for considering the flow restriction provided by, e.g. a laminar airflow "filter" or grid or nozzle openings. The distribution zone 60 may extend substantially along a dimension of the carriage 16, for example its length and/or its width.

In one example, not further shown in detail, a laminar air filter is provided to be arranged downstream the distribution zone. At least a part of a downstream side of the laminar air filter, e.g. the complete lower surface, forms the plurality of air outlets.

Figure 3:
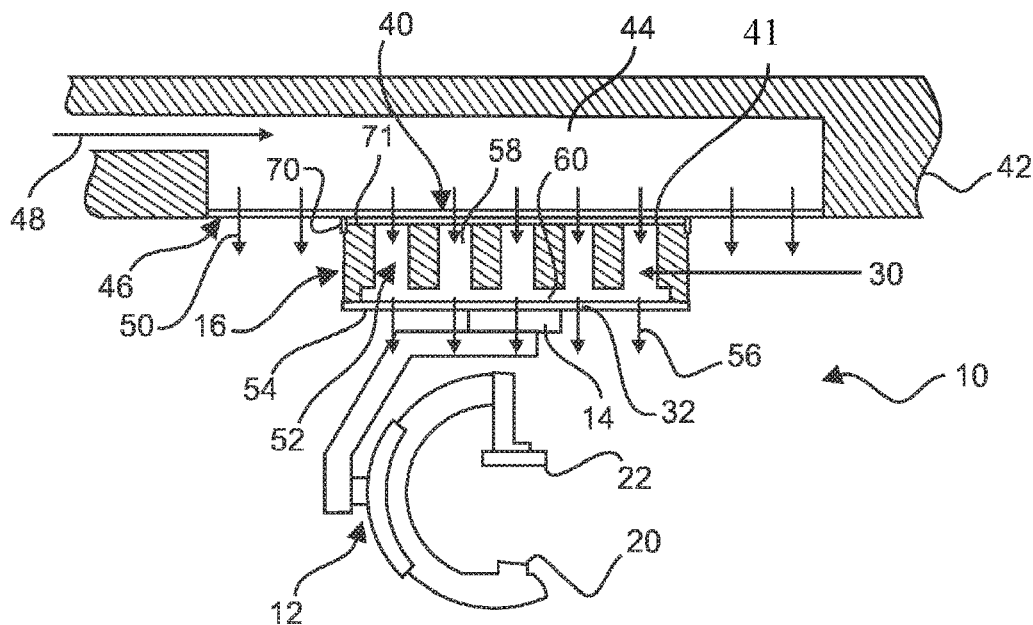
FIG. 3 shows a schematic cross-section through an example of a part of a medical imaging system.

For example, FIG. 3 shows that the air inlet 40 is arranged on an upper side 42-41 of the carriage 16. In FIG. 3, the carriage 16 is schematically shown below a ceiling 42. The X-ray image acquisition device 12 is mounted to the equipment-carrying device 14, which itself is suspendably mounted to the carriage 16. The carriage 16 is further mounted or supported by a rail arrangement, which is not further shown.

The ceiling 42 is provided with an air-supply arrangement in form of a hollow space 44 inside the ceiling. The lower side of the hollow space 44 is closed with a filter structure 46. An air-supply channel 48 is provided for feeding in supply-air that is then distributed across the hollow space 44 and provided as a downflow air, as indicated with a plurality of arrows 50. An arrow is shown in the air-supply channel 48 indicating the air inlet or feed or supply or source of the air supply 30. Since the carriage is provided with the air inlet 40, treated air is provided from a plurality of air outlets, for example provided by the outlets in form of the filter structure 46 in the ceiling structure above the medical X-ray imaging arrangement 10.

The air from the hollow space 44 is also provided to the air-supply 30 of the movable carriage 16. An airflow passage 52 is provided inside the carriage 16 between the air inlet 40 and the plurality of air outlets 32, for example provided by a further filter structure 54. The resulting laminar flow is indicated with further downflow arrows 56.

The arrows 50 and the arrows 56 thus indicate the resulting flow of air that is provided as laminar downflow for the operating zone.

For example, the hollow space 44 of the ceiling structure is also referred to as a plenum. The ceiling structure relates to a ceiling with air-supply, e.g. supply-air conduits acting as air-feed, e.g. connected to an air-conditioning device, i.e. a device for treating and preparing air in a manner that the air can be used in an operating environment, i.e. in an interventional or surgical environment.

The term "airflow passage" relates to a hollow structure, or hollow section, inside the carriage 16, which structure allows the air flowing through the airflow passage from a passage inlet to a passage outlet.

The "upper side" relates to the top side or upper surface of the carriage, i.e. the surface that faces upwards, i.e. away from the operating zone, i.e. towards the ceiling.

In an example, the carriage comprises an adaptive air inlet and the carriage with the air outlets is provided as a movable diffuser for providing a laminar downflow of supply air for the operating zone.

The term "downflow" relates to a flow (of air) in a downward manner. Downward relates to the normal situation in a room and relates to the direction of gravity.

As indicated in FIG. 3, a plurality of passageways 58 is provided, together with the distribution zone 60. The air inlet comprises, as indicated above, a plurality of inlets and the passageways 58 are connected to the inlets. The passageways discharge into the distribution zone 60 and the distribution zone 60 connects the passageways 58 with the plurality of air outlets 32.

Figure 4:
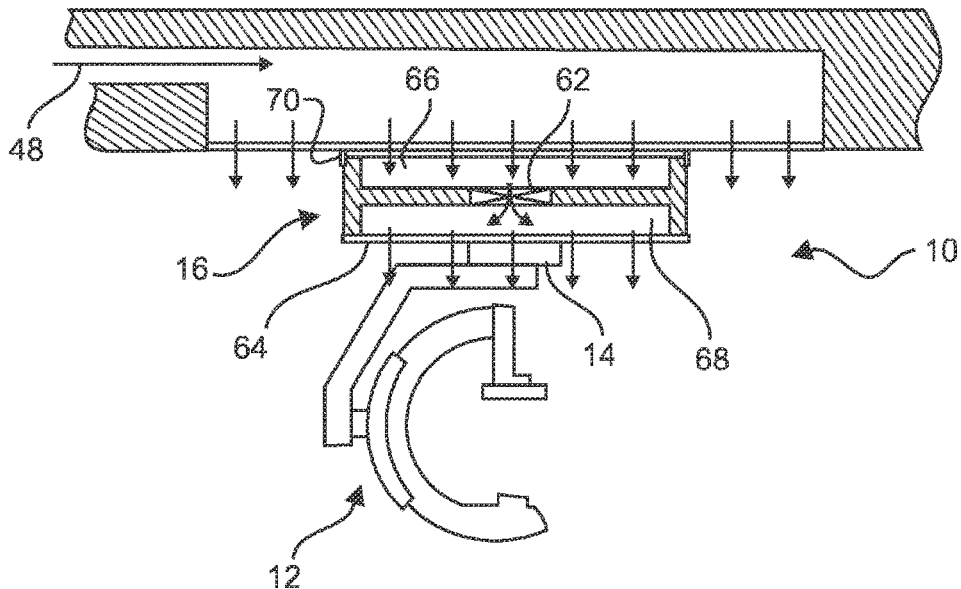
FIG. 4 shows a further example of a part of a medical imaging system.

FIG. 4 shows an example, in which the carriage 16 comprises a larger air inlet on the upper surface. In the passageway, a ventilation device 62 is provided to support the airflow from the air inlet to the plurality of air outlets, for example provided by a filter arrangement on the lower side, as indicated with reference numeral 64. A first distribution zone 66 may be provided between the air inlet and the ventilation device 62, and a second distribution zone 68 may be provided between the ventilation device 62 and the filter structure 64.

It is noted that the ventilation device 62, for example a fan, may also be provided in relation with the above-mentioned example of FIG. 3.

As a further option, shown schematically in FIG. 3 and FIG. 4 as an option, a sealing 70 is provided attached to an edge region 71 of the upper side of the carriage 16. The sealing 70 is further explained also in relation with FIGS. 6A and 6B (see below).

Figure 5:
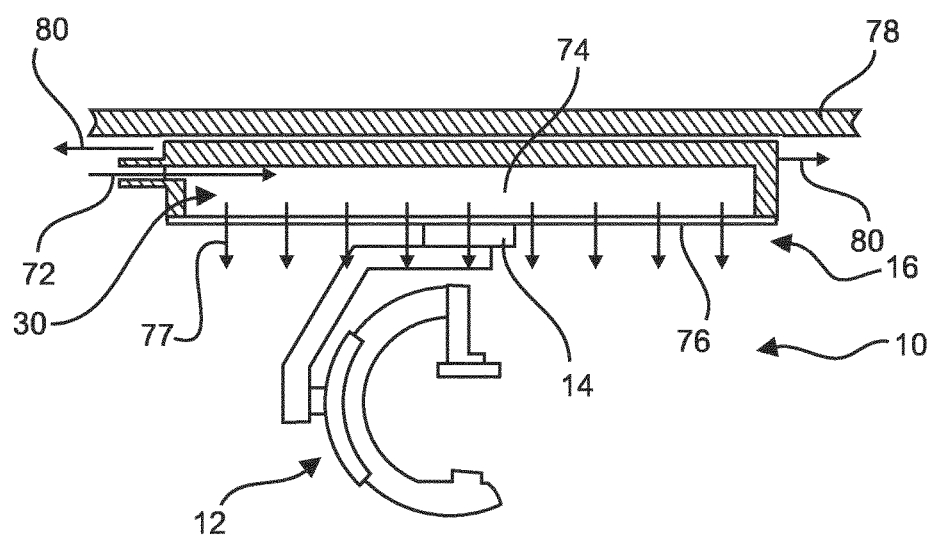
FIG. 5 shows a still further example of a part of a medical imaging system.

FIG. 5 shows a further example, according to which the carriage 16 comprises an air inlet conduit 72 for connection with the air-feed. An arrow is shown in the air inlet conduit 72 indicating the air inlet or feed or supply or source of the air supply 30. The carriage 16 comprises an air distribution zone 74 arranged as a passageway between the air inlet conduit 72 and the plurality of air outlets, for example provided by a further filter structure 76. The resulting air flow is indicated with arrows 77. The term "air inlet conduit" relates to a pipe, channel or tube, through which the treated air can pass.

As an example, shown in FIG. 5 as an option, a ceiling 78 may thus be provided without any air-supply and the carriage 16 is provided with a larger dimension instead and equipped with the separate air inlet conduit 72. Even though the carriage 16 is arranged movably in relation to the ceiling 78, as indicated with movement arrows 80, a sufficiently large carriage laminar flow zone is provided to cover the operating zone in a sufficient manner.

As an option, the carriage is provided with a horizontal extension that defines the maximum size of the flow zone for air-supply of an operating zone. In an example, the carriage is provided to extend over at least twice the dimensions of a standard patient table, i.e. at least 2 m×3 m.

Figure 6A:
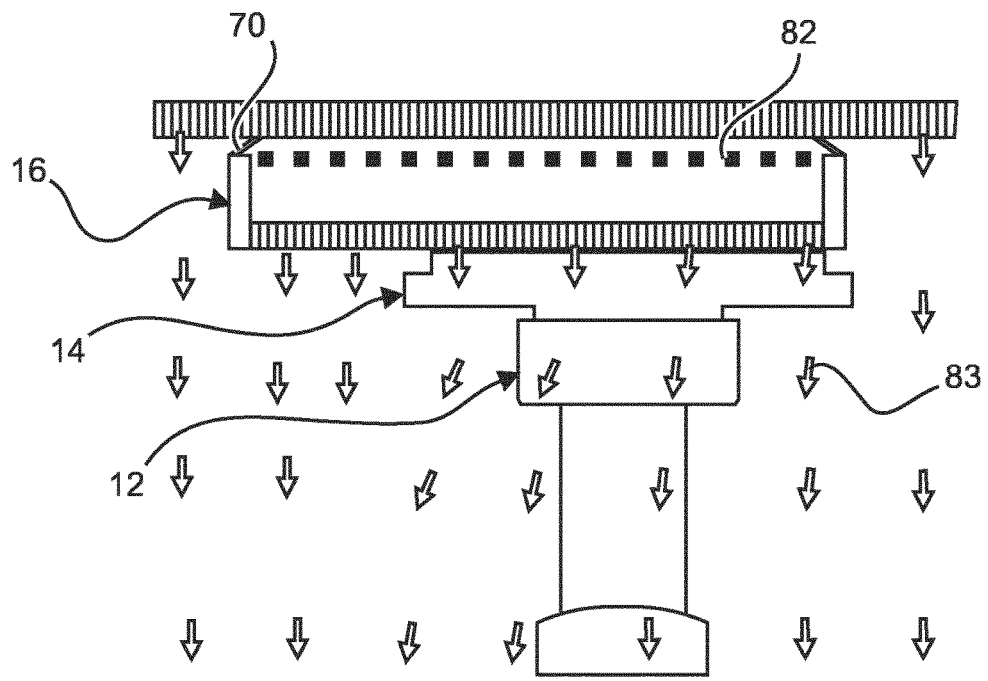
FIGS. 6A and 6B show an example of a further detail as an option for the medical X-ray imaging arrangement.
Figure 6B:
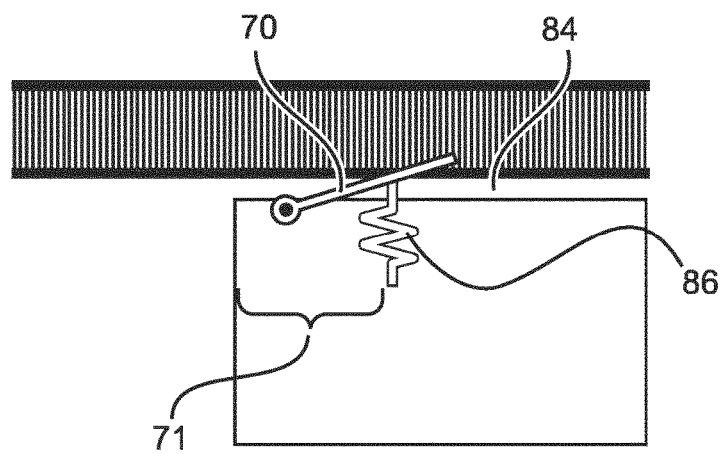

FIG. 6A shows a schematic setup of an example with the movable carriage 16 and the equipment-carrying device 14, as well as the X-ray image acquisition device 12 schematically indicated. FIG. 6B shows the detail in a larger illustration. In the example, supply-air is provided by a ceiling structure, and respective air inlets 82 are indicated.

In an example, the closure of the air gap (see FIG. 6B) is provided to be controlled in an active manner such that the air gap is closed only when the carriage is not moving.

The resulting air flow for the operating zone is indicated with arrows 83.

As an option, the above-mentioned indicated sealings 70 are provided attached to the end region 71 of the upper side of the carriage 16. The sealing 70 is configured to close an air gap 84 between the carriage 16 and the ceiling structure comprising the supply-air outlets. Preferably, the sealing 70 is movable to adjustably close or open the air gap.

For example, the sealing 70 can be biased to abut or touch the ceiling structure, as indicated with spring symbol 86.

For example, the sealing 70 comprises an arrangement of strips, which automatically flip up to close the air gap between the air-supply source and the rail carriage, e.g. by a resilient mechanism. When the rail carriage 16 is moving along the rail arrangement, the strips can be pulled down, e.g. by a controlled magnet or other actuator.

The term "movable" relates to a sealing 70 that has a movable, i.e. an adaptable edge. The whole sealing may be movable. In another option, the sealing is changeable in its size to result in a "moving" front edge that closes the gap. For example, an inflatable sealing may be provided.

Figure 7A:
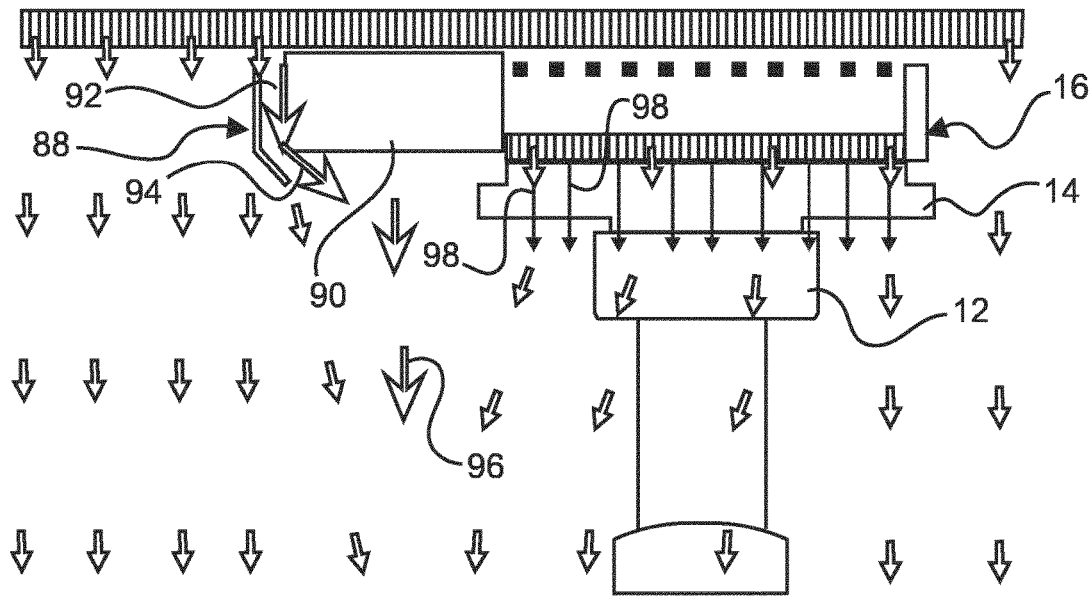
FIGS. 7A and 7B show another example of a still further detail as a further option for the medical X-ray imaging arrangement.
Figure 7B:
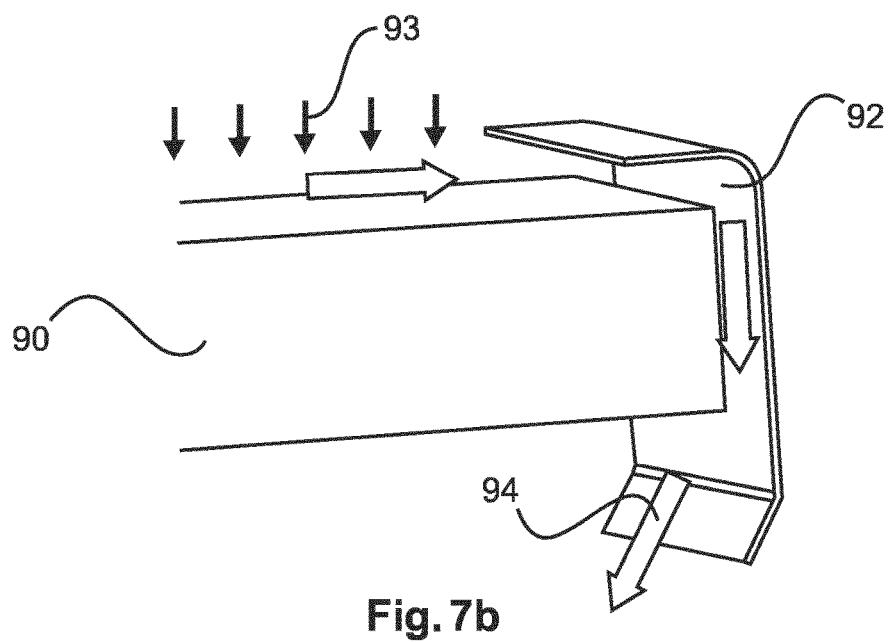

FIG. 7A shows a further example provided also as an option in combination with the above-mentioned examples. The carriage 16 comprises at least one side skirt air-guiding device 88 that is configured, in one example, to guide treated air from above the carriage towards the laminar downflow provided by the plurality of air outlets. FIG. 7B shows the detail in a larger illustration in a perspective view.

In an example, the carriage 16 has an airtight (closed) frame portion 90 and supply-air from above the carriage is guided to circumvent the closed portion 90 such that an airflow channel 92, as indicated in FIG. 7B, is formed in-between to guide the supplied air received from above, for example from air outlets in a ceiling structure, the air from above indicated with arrows 93, in order to have the air bypassing the closed portion forming a downflow stream 94.

In another example, the carriage comprises a closed system and supply-air from above the carriage is guided by the side skirts to guide airflow downwards into a pressure chamber (i.e. distribution zone) for an even distribution and an air-supply via a plurality of openings to obtain a downflow in the area underneath the frame mount comprising the closed system.

The so-to-speak additional airflow provided by the side skirt air-guiding device 88 is indicated with additional flow arrows 96 in FIG. 7A.

In an example (not shown), the at least one side skirt air-guiding device 88 is configured to guide treated air from above the carriage towards the air inlet for supplying the air to the distribution zone.

In an example, the carriage 16 is a closed system and the side skirt air-guiding device 88 is provided on one or more sides of the carriage 16 to arrange for the air supply by guiding air from above to the air inlet to circumvent the carriage such that the airflow channel 92 is formed in-between to guide the supplied air received from above for supplying air to the distribution zone. The distribution zone and also the laminar air filter are arranged below the (closed) carriage. Hence the air is bypassing the closed carriage. This allows to form the laminar downflow by the distribution zone below the carriage and to generate the laminar downflow.

As a further option, also indicated in FIG. 7A, an equipment-carrying device 14 is used and provided with an airflow passage 98 and air outlets on its lower side. In an example, the equipment-carrying device 14 comprises a turntable-shaped rotating bearing and an airflow passage is provided through the turntable-shaped rotating bearing.

In an example, the downflow filter is provided on the inner (upper) side of the bottom side of the carriage. The downflow filter creates a pressure inside the airflow passage such that the velocity of the downflow can be optimized in dependency of the size. The filter can be a woven filter or perforated plate. In addition, these filters may be accessible from the outside such that the replacement or cleaning over time is possible.

In an example, the X-ray image acquisition device (or X-ray imaging system) comprises the at least one X-ray source and an X-ray detector, as indicated above. The X-ray detector can be attached to and supported by the equipment-carrying device. In another example, the X-ray detector is provided as a portable detector, which is provided independently of the equipment-carrying device 14.

According to an example, as indicated in FIG. 1, the X-ray imaging system comprises a C-arm X-ray device and the C-arm is movably mounted to the equipment-carrying device.

The C-arm X-ray device comprises a C-arm with an X-ray source and an X-ray detector mounted to its opposite ends. The C-arm is movably mounted to the equipment-carrying device. The C-arm can be rotatably mounted around one axis or more than one axis. The C-arm can be mounted to the equipment-carrying device with a sleeve support, allowing a rotational movement of the C-arm in form of the sliding movement along the sleeve in the circular direction of the C-arm. The sleeve support can be mounted to be rotatable in relation to the C-arm.

In another example, other types of X-ray imaging systems can be provided, such as robotic arms or an X-ray source suspended by a vertical telescopic arm support.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfill the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. A medical X-ray imaging arrangement, comprising:
   an X-ray image acquisition device;
   a movable carriage including a sealing; and
   an air-supply for an operating zone,
   wherein the movable carriage is movably mountable to a ceiling structure of an operating room, wherein the X-ray image acquisition device is movably mountable to the movable carriage for acquiring image information of an object, wherein the air-supply comprises a plurality of air outlets provided on a bottom side of the movable carriage arranged to provide treated air from an air-feed as a primary laminar downflow defining a carriage laminar flow zone for the operating zone, and wherein the sealing is configured to automatically open an air gap between the movable carriage and a ceiling structure when the movable carriage is moving.

2. The medical X-ray imaging arrangement according to claim 1, wherein the movable carriage comprises:
an air inlet connectable to the air-feed; and
a distribution zone;
wherein the distribution zone is a hollow space that extends transverse to a flow direction and connects the air inlet with the plurality of air outlets.

3. The medical X-ray imaging arrangement according to claim 2, wherein the air inlet is provided to be arranged on an upper side of the movable carriage,
wherein the air inlet comprises a plurality of inlets configured to receive the treated air from a plurality of supply-air outlets provided in a ceiling structure above the medical X-ray imaging arrangement,
wherein an airflow passage comprising a plurality of passageways is provided inside the movable carriage in connection with the air inlets, and
wherein the distribution zone connects the passageways with the plurality of air outlets, the passageways discharging treated air into the distribution zone.

4. The medical X-ray imaging arrangement according to claim 2, wherein a laminar air filter is provided to be arranged downstream the distribution zone, and wherein at least a part of a downstream side of the laminar air filter forms the plurality of air outlets.

5. The medical X-ray imaging arrangement according to claim 4, wherein the discharge zone extends substantially along a dimension of the movable carriage.

6. The medical X-ray imaging arrangement according to claim 2, wherein the movable carriage comprises at least one side skirt air-guiding device, and
wherein the at least one side skirt air-guiding device is configured to guide treated air from above the movable carriage:
towards the laminar down flow provided by the plurality of air outlets; and/or
towards the air inlet for supplying the air to the distribution zone.

7. The medical X-ray imaging arrangement according to claim 2, wherein, as the air inlet, the movable carriage comprises an air inlet conduit for connection with the air-feed, and
wherein the movable carriage comprises an air distribution zone arranged as a passageway between the air inlet conduit and the plurality of air outlets.

8. The medical X-ray imaging arrangement according to claim 1, wherein the sealing is provided attached to an edge region of the upper side of the movable carriage, and
wherein the sealing is configured to close the air gap between the movable carriage and a ceiling structure when the movable carriage is mounted to the ceiling structure.

9. The medical X-ray imaging arrangement according to claim 8, wherein the sealing is movable to adjustably close or open the air gap.

10. The medical X-ray imaging arrangement according to claim 1, wherein a ventilation device is provided in the airflow passage within the movable carriage to support the airflow from the air inlet to the plurality of air outlets.

11. The medical X-ray imaging arrangement according to claim 1, further comprising:
an equipment-carrying device,
wherein the equipment-carrying device is provided with an airflow passage and air outlets on its lower side.

12. The medical X-ray imaging arrangement according to claim 1, wherein the X-ray image acquisition device comprises a C-arm X-ray device, and
wherein the C-arm X-ray device is movably mounted to the movable carriage.

13. The medical X-ray imaging arrangement of claim 1, wherein the sealing is resiliently movable to adjustably close or open the air gap.

14. The medical X-ray imaging arrangement of claim 1, wherein the sealing comprises an arrangement of strips which automatically flip up to close the air gap.

15. The medical X-ray imaging arrangement of claim 1, wherein the sealing is biased to touch the ceiling structure to close the air gap when the movable carriage is mounted to the ceiling structure.

16. The medical X-ray imaging arrangement of claim 1, wherein the sealing is biased to touch the ceiling structure to close the air gap when the movable carriage is stationary.

17. The medical X-ray imaging arrangement of claim 1, wherein the sealing has a changeable size.

18. A medical imaging system, comprising:
a medical X-ray imaging arrangement;
a patient support; and
a rail arrangement;
wherein the medical X-ray imaging arrangement comprises an X-ray image acquisition device; a movable carriage including a sealing; and
an air-supply for an operating zone,
wherein the movable carriage is movably mountable to a ceiling structure of an operating room,
wherein the X-ray image acquisition device is movably mountable to the movable carriage for acquiring image information of an object,
wherein the air-supply comprises a plurality of air outlets provided on a bottom side of the movable carriage arranged to provide treated air from an air-feed as a primary laminar downflow defining a carriage laminar flow zone for the operating zone,
wherein the sealing is configured to automatically open an air gap between the movable carriage and a ceiling structure when the movable carriage is moving,
wherein the rail arrangement is arranged overhead and disposed above the patient support, and
wherein the movable carriage of the medical X-ray imaging arrangement s movably mounted along the rail arrangement.

19. The medical imaging system according to claim 18, wherein a ceiling region above at least a part of the rail arrangement is provided as the air-feed and comprises a plurality of supply-air outlets.

20. The medical imaging system according to claim 19, wherein the ceiling region with the supply air outlets is larger than the movable carriage, which is movable in relation to the ceiling,
wherein the movable carriage is arranged below the ceiling partly masking the supply air outlets of the ceiling structure, wherein unmasked supply air outlets act as ceiling air outlets,
wherein the ceiling air outlets provide a secondary laminar downflow defining an additional laminar flow zone for the operating zone, and
wherein the movable carriage laminar flow zone and the additional laminar flow zone provide a laminar downflow covering the operating zone.

\* \* \* \* \*